(12) United States Patent
Yamazaki (10) Patent No.: US 12,121,716 B2
(45) Date of Patent: *Oct. 22, 2024

(54) COSMETIC MASK

(71) Applicant: YA-MAN LTD., Tokyo (JP)

(72) Inventor: Iwao Yamazaki, Tokyo (JP)

(73) Assignee: YA-MAN LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,121

(22) Filed: May 30, 2023

(65) Prior Publication Data

US 2023/0347137 A1 Nov. 2, 2023

Related U.S. Application Data

(63) Continuation of application No. 16/763,536, filed as application No. PCT/JP2018/037455 on Oct. 5, 2018, now Pat. No. 11,691,002.

(30) Foreign Application Priority Data

Nov. 13, 2017 (JP) ................... 2017-217902

(51) Int. Cl.
*A61N 1/05* (2006.01)
*A61N 1/36* (2006.01)
*A61N 7/00* (2006.01)

(52) U.S. Cl.
CPC ............. *A61N 1/0526* (2013.01); *A61N 1/36* (2013.01); *A61N 7/00* (2013.01); *A61N 2007/0034* (2013.01)

(58) Field of Classification Search
CPC ..... A61N 1/0526; A61N 1/328; A61N 1/0476
See application file for complete search history.

(56) References Cited

U.S. PATENT DOCUMENTS

| | | | | |
|---|---|---|---|---|
| 3,279,468 A | * | 10/1966 | Le | A61N 1/0456 607/140 |
| 3,447,537 A | * | 6/1969 | King | A61N 1/321 607/140 |
| 5,527,357 A | * | 6/1996 | Springer, Jr. | A61N 1/326 607/140 |

(Continued)

*Primary Examiner* — George R Evanisko
(74) *Attorney, Agent, or Firm* — Bayramoglu Law Offices LLC (57) ABSTRACT

[Problem] To provide a cosmetic mask which imparts effective stimulation to the appropriate position and has a tightening effect. [Solution] This cosmetic mask is worn on the face of a user, is able to cover at least the cheeks, and is equipped with a pair of simulators which impart electric or ultrasonic stimulation to a location corresponding to either the zygomatic muscle or masseter muscle of the user. The cosmetic mask may be equipped with a stimulator fitting unit for fitting the stimulators to a cheek position, and maybe constituted so that at least some of the stimulators are detachable. The cosmetic mask may also be equipped with a nosepiece which matches the protruding shape of the nose, a left-right fitting portion which is fitted while applying tensile force to the left and right sides of the face, and a vertical fitting portion which is fitted while applying tensile force from the lower surface of the mandible over both sides of the face to the top of the head.

9 Claims, 10 Drawing Sheets

(56) References Cited

U.S. PATENT DOCUMENTS

| | | | | |
|---|---|---|---|---|
| 2002/0161416 A1* | 10/2002 | Huang | ............... | A61N 1/0452 |
| | | | | 607/48 |
| 2014/0350442 A1* | 11/2014 | Park | ............... | A61N 1/322 |
| | | | | 601/48 |
| 2018/0099143 A1* | 4/2018 | Kim | ............... | A61N 1/0492 |

\* cited by examiner

COSMETIC MASK

CROSS REFERENCE TO THE RELATED APPLICATIONS

This application is a continuation of U.S. patent application Ser. No. 16/763,536, filed on May 12, 2020, and titled "Cosmetic Mask", which is a 371 National Stage Application of International Application No. PCT/JP2018/037455, filed on Oct. 5, 2018, which is based upon and claims priority to Japanese patent application No. 2017-217902, filed on Nov. 13, 2017, and the entire contents of each of the foregoing applications are incorporated herein by reference.

TECHNICAL FIELD

The present invention relates to the field of a cosmetics, specially relates to a mask that is worn on a user's face that uses technology for effectively applying stimulation to appropriate parts of the face.

BACKGROUND

A mask for applying electrical stimulation to various anterior muscles of a user is conventionally known. For example, Japanese domestic patent publication WO2016-009643 discloses a cosmetic mask that is provided with a mask body that covers the face, the mask body being formed of silicone, having openings at positions of the eyes, nose, and mouth, and having electrode portions on inner surfaces of the mask body.

Also, Japanese laid-open patent publication No. 2017-108758 discloses technology that provides an elastic base material that covers the face, the elastic base material being formed of silicone, with openings at positions of the eyes, nose, and mouth, and having stimulation electrodes at points here electrical stimulation is applied, and it is described that this is effective in lifting up sagging face muscles.

Japanese laid open patent publication No. 2013-081606 discloses a beauty appliance that is provided with a treatment member that covers the face. It is described that the treatment member has a cover section made of silicone, a conductive member with electrodes formed around the cheeks, and openings at positions of the eyes, nose, and mouth.

Utility Model Publication No. 3082187 describes a treatment mask provided with a mask body that covers the face, and that has openings at positions of the eyes, nose, and mouth, and electrodes at inner surfaces of the mask body. It is described that the mask body is formed of a silicone rubber material, and that uniform adhering to the skin is achieved by the mask body deforming under its own weight.

With the above described prior arts, although it is known to provide electrodes that apply electrical stimulation generally around the cheeks, there is no idea of adapting it to positions and characteristics of individual muscles. There was a particular risk that electrodes for cheek areas would be either too large or would apply inappropriate stimulation. Further, a proper tightening effect using elasticity of the mask is not provided when wearing it, and a mask that combines fit and a tightening effect is not provided. Also, sufficient research regarding the optimal stimulation for each facial muscle has not been conducted.

PRIOR ART PUBLICATIONS

Patent Publications

Patent Publication 1: Japanese Domestic Republication of WO2016-009643; Patent

Publication 2: Japanese laid open patent publication No. 2017-108758;

Patent Publication 3: Japanese laid open patent publication No. 2013-081606;

Patent Publication 4: Utility Model Publication No. 3082187.

SUMMARY

Problems to be Solved by the Invention

With the above described prior arts, although it is known to provide electrodes that apply electrical stimulation generally around the cheeks, there is no method of adapting it to positions and characteristics of individual muscles. There was a particular risk that electrodes for cheek areas would be either too large or would apply inappropriate stimulation. Further, a proper tightening effect using elasticity of the mask is not provided when wearing it, and a mask that combines fit and a tightening effect is not provided. Also, sufficient research regarding the optimal stimulation for each facial muscle has not been conducted.

Means for Solving the Problems

In order to solve the above described problems, the present invention provides a cosmetic mask as described in the following.

In one embodiment, the cosmetic mask is worn on the face of a user that covers at least the user's cheeks, the cosmetic mask is provided with a pair of simulators that apply electrical or ultrasound stimulation to locations corresponding to at least one of the zygomatic muscles or masseter muscles of the user.

In one embodiment, the above-mentioned cosmetic mask is provided with stimulator fitting sections for fitting the stimulators at positions of the cheeks, and at least some of the stimulators are made detachable.

In one embodiment, the above-mentioned cosmetic mask is provided with a nosepiece that conforms to at least the convex shape of a nose.

In one embodiment, the above-mentioned cosmetic mask is provided with horizontal fitting sections that are fitted while applying tensile force toward left and right sides of the face.

In one embodiment, the above-mentioned cosmetic mask is provided with vertical fitting sections that are fitted while applying tensile force from lower surfaces of the lower mandible along both sides of the face towards the top of the head.

In one embodiment, the above-mentioned stimulators are mounted to apply electrical stimulation, and it is preferable for the above-mentioned electrical stimulation to be applied at a frequency of between 2 Hz and 100 Hz.

In one embodiment, the above-mentioned electrical stimulation that is applied to the zygomatic muscles is preferably at a frequency of between 2 Hz and 20 Hz.

In one embodiment, the above-mentioned electrical stimulation that is applied to the masseter muscles is preferably at a frequency of between 20 Hz and 100 Hz.

In one embodiment, a cosmetic mask is provided wherein the above-mentioned stimulators that apply electrical stimulation comprise a detachable current generator that generates electrical current, and electrodes that are provided on the mask, with a control section for controlling current, a feed section for feeding electricity, and mask-side electrodes for passing electricity to electrodes of the cosmetic mask being provided in the current generator, and the cosmetic mask being provided with a skin side electrode that contacts the skin, and a device-side electrode that is electrically connected to the current generator.

In one embodiment, the stimulators for applying electrical stimulation are equipped with both a zygomatic muscle stimulator and a masseter muscle stimulator for applying stimulation to the zygomatic muscles and the masseter muscles, and the above-mentioned control section may feed respectively different electrical currents to the zygomatic muscle stimulator and the masseter muscle stimulator.

In one embodiment, the above-mentioned cosmetic mask of any one of claim 1 to claim 9 is formed integrally using a resin material, and hardness of material is varied in accordance with location.

In one embodiment, hardness of material may be formed relatively harder for locations corresponding to facial surfaces of the above-mentioned cosmetic mask than for the above-mentioned horizontal fitting sections.

In one embodiment, hardness at locations corresponding to facial surfaces of the above-mentioned cosmetic mask may be formed of a material that is relatively harder than the above-mentioned vertical fitting sections.

Effect of the Invention

As a result of the above described embodiments, the present invention provides the following effects. Specifically, while detachable stimulators are mounted on appropriate positions of the cosmetic mask, a pair of stimulators that apply electrical or ultrasonic stimulation can perform treatment to locations that correspond to zygomatic muscles of a user, that have a high cosmetic effect. In particular, by applying electrical stimulation to zygomatic muscles there is an effect of developing muscles that lift flabby cheeks and laughter lines.

Further, using a pair of masseter muscle stimulators that apply electrical or ultrasonic stimulation to locations corresponding to masseter muscles of the user, treatment on the masseter muscles having a high cosmetic effect can be performed. In particular, stimulation to the masseter massages and relieves them, and has the effect of providing a well-shaped and sharp face line.

The horizontal fitting sections and vertical fitting sections of the present invention enable the jaw line, mouth, and face line to be physically raised and form a sharp face line. In particular, it is possible to perform optimum treatment by applying stimulation while keeping such face lines.

Forming the cosmetic mask integrally and changing hardness of material in accordance with locations makes it easy to fit to facial surfaces and contributes to improvement in face line by applying moderate tensile force.

DESCRIPTION OF THE NUMERALS

1 mask body
10 mask section
11 horizontal band
12 vertical band
13 upper edge section
14 nosepieces
15 mouth opening
16 stimulator fitting section

DETAILED DESCRIPTION OF THE EMBODIMENTS

Embodiments of the present invention will be described in the following, based on practical examples shown in the drawings. Implementations of the invention are illustrated below by way of specific examples, and those skilled in the art can easily understand other advantages and effects of the invention from the content disclosed in this description. The invention can also be implemented or applied through other different specific embodiments, and various details in this description can also be modified or changed based on different viewpoints and applications without departing from the spirit of the invention. It should be noted that the embodiments are not limited to those described below.

A cosmetic mask of the present invention is a cosmetic mask that is worn on the face of a user, the cosmetic mask is configured to as to cover at least the cheeks. A nosepiece that conforms to the convex shape of the nose is preferably provided for convenience of positioning, and besides this nose piece it is also possible to provide openings for the mouth, eyes, and ears. For example, the cosmetic mask is preferably made of an elastic material such as silicone or natural rubber. In particular, silicone has tightening strength, and it is most suitable for being used in contact with the skin because it is often utilized for medical purposes.

A cosmetic mask, characterized by being provided with either or both of a pair of zygomatic muscle stimulators for applying electrical or ultrasound stimulation to locations corresponding to the zygomatic muscles of the user, and a pair of masseter muscle stimulators for applying electrical or ultrasonic stimulation to sides corresponding to masseter muscles, while being adjusted at appropriate positions on the face using the nosepiece, and the openings, corresponding to the mouth, eyes, and ears, is provided.

A pair of stimulators for applying stimulation to the zygomatic muscles and masseter muscles, and stimulator fitting sections for fitting the stimulators to positions of the cheeks are provided on the cosmetic mask, and the cosmetic mask is configured so that at least some of the stimulators can be detached from the cosmetic mask.

With the practical examples below, although stimulators that are provided with electrodes that apply electrical stimulation to both zygomatic muscles and masseter muscles are shown, the embodiment is not thus limited. Although an example where some of the stimulators are detachable is shown, the stimulators do not need to be of a detachable type.

Also, although description has been given for a zygomatic muscle stimulator and masseter muscle stimulator that are configured to apply electrical stimulation, it is also possible to apply ultrasound stimulation as a well-known beauty treatment, and the stimulators of the present invention may be configured to use ultrasound. The cosmetic mask may also be configured to perform both electrical stimulation and ultrasound stimulation treatment.

Figure 1:
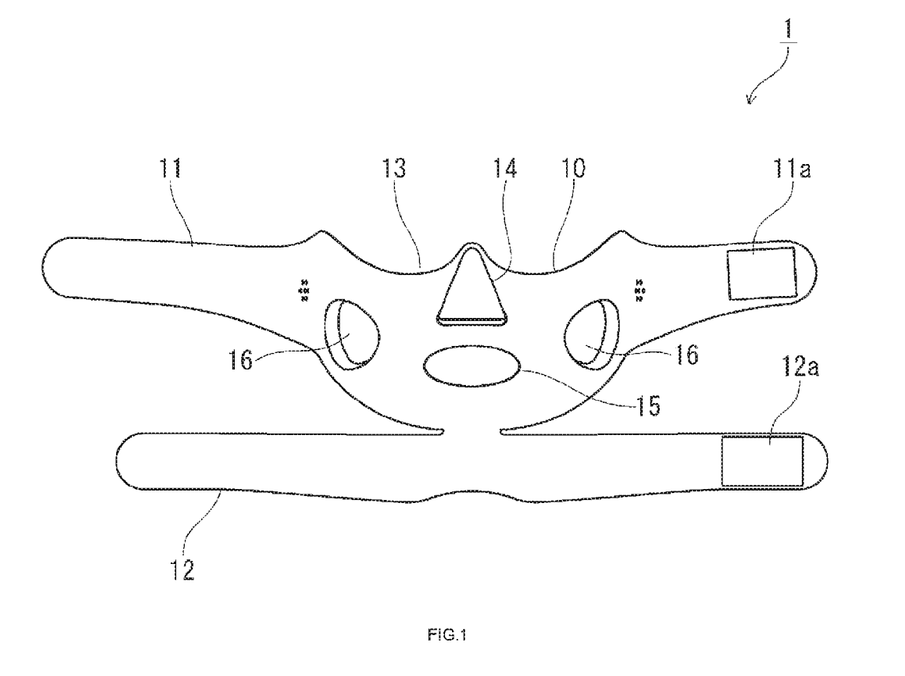
FIG. 1 is a front view of a mask body of the present invention.
Figure 2:
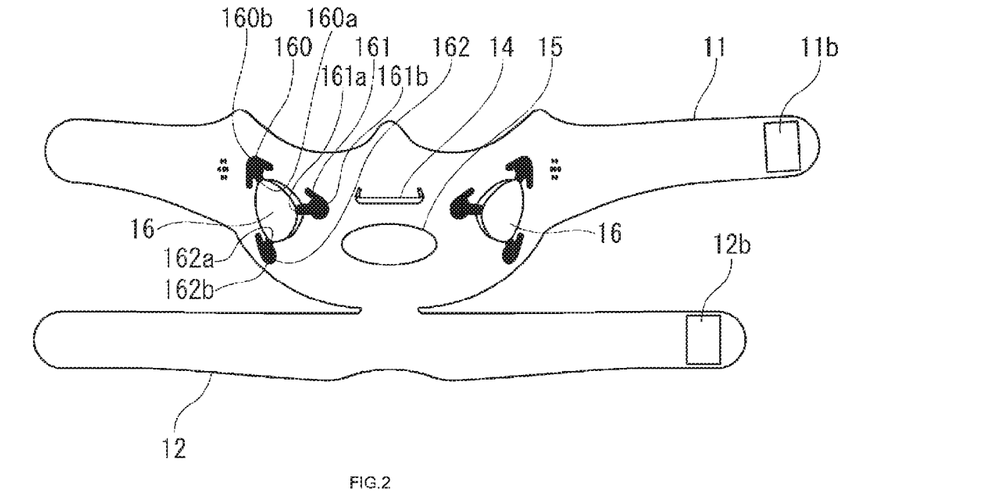
FIG. 2 is a rear view of a mask body of the present invention.

FIG. 1 and FIG. 2 depict the front view and the rear view of a mask body (1) of the present invention are respectively shown in FIG. 1 and FIG. 2. The mask body (1) is an elastic body that is integrally formed of silicone, and forms a mask section (10) that covers a lower half of the user's face from the user's eyes to the jaw, a horizontal band (11) which is a lateral fitting part that is provided extending in a lateral of the mask section (10), and a vertical band (12) which is a vertical fitting part that is connected to a lower end of the mask section (10) and is provided extending in the left and right directions when it is opened.

An upper edge section (13) that is formed in a concave shave so as to avoid contact with the eyes, a nosepiece (14) that is formed protruding three-dimensionally in conformity with the shape of the nose, and a mouth opening (15) that is opened to expose the mouth, are formed in the mask section (10).

The mask body (1) can be worn naturally by the user adjusting the nosepiece (14) and the mouth opening (15).

The nosepiece (14) may be configured to have a cutting that allows the nostrils to be exposed when wearing the mask, and through which the user's nose tip will protrude.

A stimulator fitting section (16) for fitting of the current generator is opened at a cheek position in the mask body (1). The stimulator fitting section (16) is not necessarily limited to being opened, as in this practical example, and engagement sections may be provided that engage with a skin side of the mask body (1), a plurality of openings may be provided to expose only the electrodes, grooves may be formed, or any other form may be used.

When adjusting the mask body (1) on the face, the mask section (10) is stretched in the lateral direction by passing the horizontal band (11) around both sides of the head and fastening hook-and-loop fasteners (11a) and (11b) at the back. In this way a tightening effect is achieved by applying moderate pressure on the face, particularly on the cheek parts.

Further, the vertical band (12) is fitted by curving from the mask section (10) at a right angle to a lower surface of the lower jaw, and passing around both sides of the head, while applying tensile force towards the top of the head. The vertical band (12) is similarly attached with hook-and-loop fasteners (12a) and (12b).

By stretching the vertical band (12), both of the vertical band (12) and the mask section (10) below the vertical band (12) lift the cheeks upward to achieve a lift-up effect.

Besides the hook-and-loop fasteners, it is also possible to use hooks and one-touch buckles, magnets, etc., to attach the horizontal band (11) and the vertical band (12).

With the present invention, the horizontal band (11) and the vertical band (12) do not necessarily need to be provided, and as another method of constructing the mask section (10), for example, the mask can be fitted to the face with a separate band. Also, as an example of a horizontal fitting part, ear openings may be made, as disclosed in FIG. 8, so that the mask can be hooked over the ears. It is also possible to not provide the vertical band, and only provide the horizontal band (11).

Figure 3:
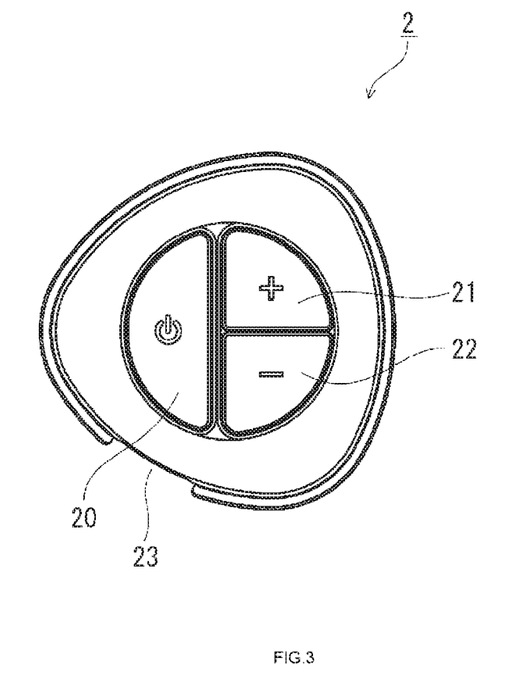
FIG. 3 is a front view of a current generator of the present invention.
Figure 4:
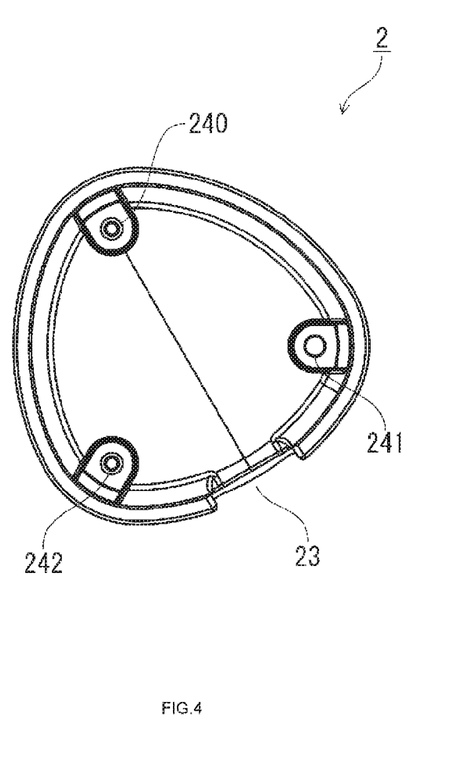
FIG. 4 is a rear view of the current generator of the present invention.
Figure 5:
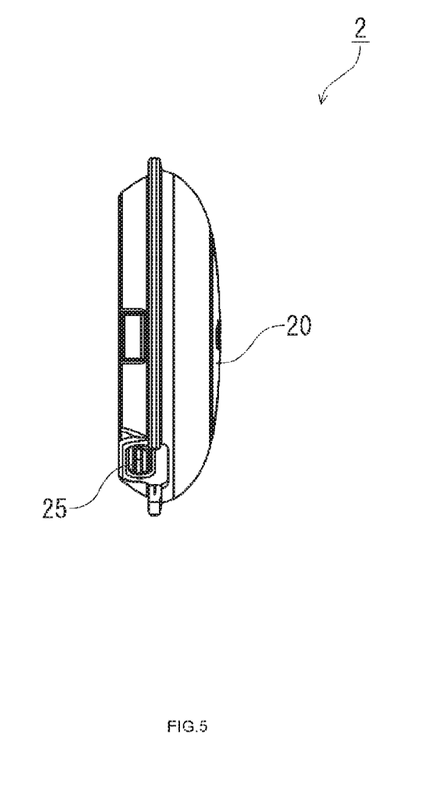
FIG. 5 is a left side view of the current generator of the present invention.

FIG. 3, FIG. 4 and FIG. 5 depict the front view, rear view, and left side view of a current generator (2) according to the present invention. The current generator (2) is a generally triangular shape comprising a power supply button (20) on a surface that constitutes an outer surface of the time of fitting, and adjustment buttons (21) and (22), and has a notch (23) formed in a part thereof.

Three mask side electrodes (240), (241), and (242) are provided on a rear surface.

The shape of the current generator (2) is not limited to being generally triangular, and may also be formed in any shape, such as a circle, an ellipse, a rectangle, or a hexagon etc. In particular, it is preferable to make the current generator a shape that is not symmetrical so that the fitting direction is clear.

With this practical example, as described above, a structure that applies electrical stimulation is shown as a stimulator, with a control section, not shown, that controls electrical current being provided inside the current generator (2), and a feed section can feed power by charging a rechargeable battery, not shown, from a feed terminal (25) that is provided in the notch (23). Such a structure enables convenient and low-cost use without a power supply cable or battery at the time of use. Naturally it is also possible to have a configuration in which power is fed from outside, or a battery is used.

Figure 6:
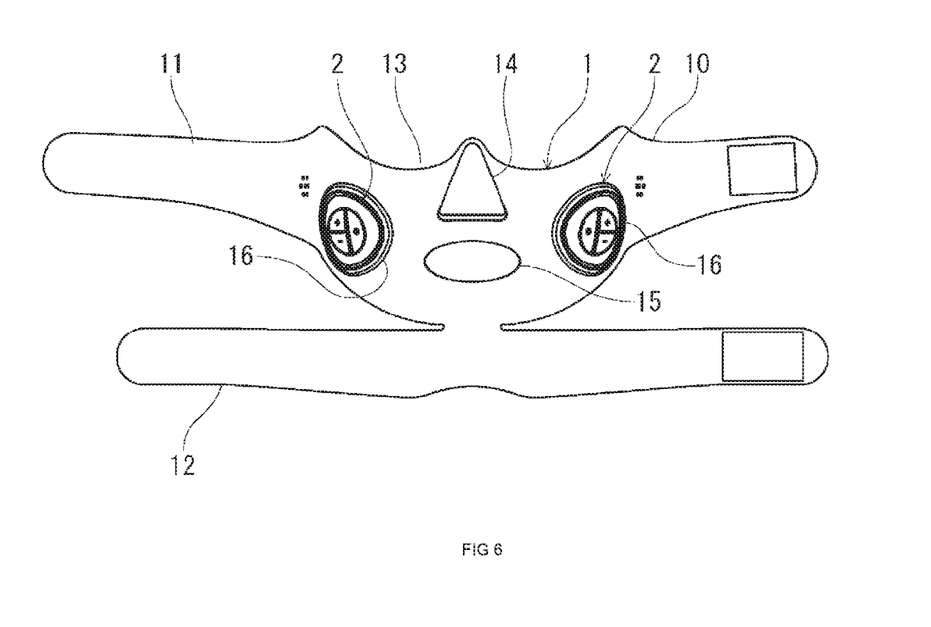
FIG. 6 is a front view of a cosmetic mask of the present invention.

FIG. 6 shows front view of the cosmetic mask according to the present invention, and depicts a state where the mask body (1) and the current generator (2) have been combined.

Convexoconcave portions that correspond to the notches (23) are formed in the stimulator fitting section (16) of the mask body (1), to regulate the orientation of the current generator (2).

Mask-side electrodes (240), (241), (242) of the current generator (2) that has been appropriately fitted are energized by being in contact with device-side electrodes (161a), (161b), (161c) that are provided on the inside of the stimulator fitting section (16).

Skin side electrodes (160b), (161b), and (162b) that are integrally formed by a conductor are exposed to the skin side, namely the rear surface of the mask body (1), from the device-side electrodes (160a), (160b) and (160c). Each of the electrodes (160), (161) and (162) constitute arrow shapes radiating out from apexes of a triangle, as shown in FIG. 2.

Figure 7:
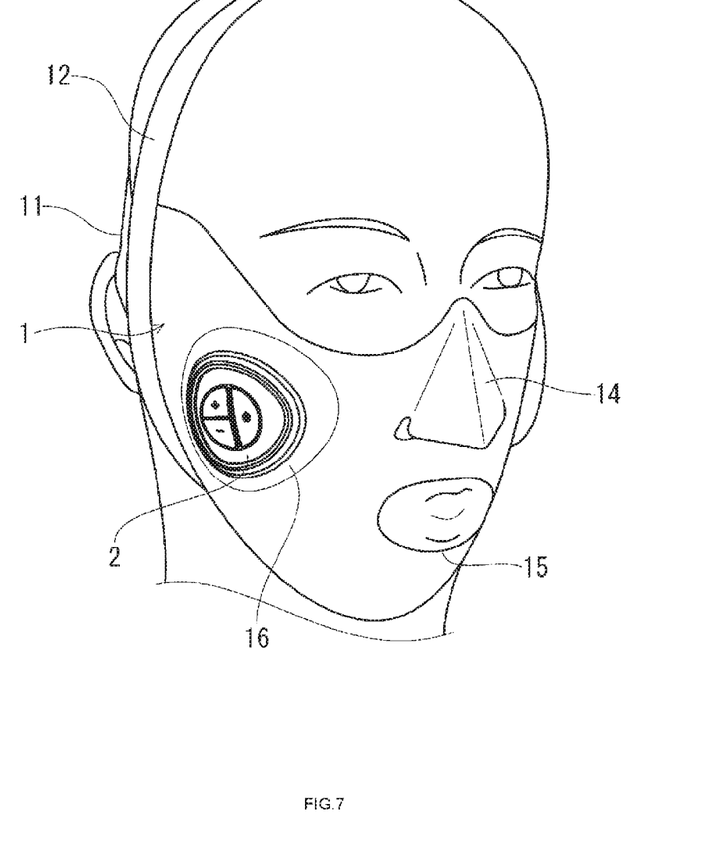
FIG. 7 is an explanatory drawing showing usage state of the cosmetic mask of the present invention.

FIG. 7 is an explanatory drawing showing usage state of the cosmetic mask of the present invention, and as has already been described the horizontal band (11) is fitted at the back of the head while the vertical band (12) is fitted at the top of the head, and it can be seen that the current generator (2) is then in precise contact with cheeks.

Figure 8:
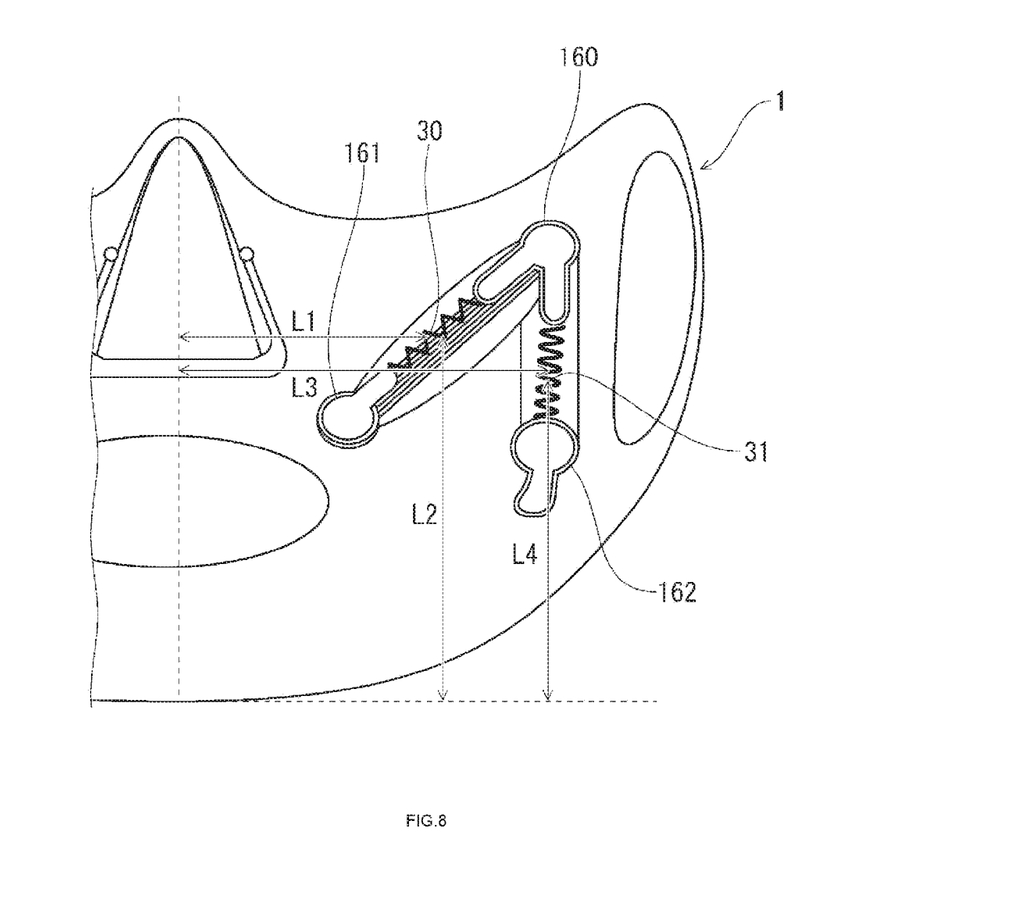
FIG. 8 is an explanatory drawing showing a relationship between positions of zygomatic muscles and masseter muscles, and electrodes.

After performing appropriate positioning as described above, respective currents are applied from each of the electrodes (160), (161), (162) to the zygomatic muscles and the masseter muscles, as shown in FIG. 8.

The zygomatic muscles have a function of lifting saggy cheeks and laugh lines. While they are classified into the greater zygomatic muscle and the lesser zygomatic muscle, with this practical example, a muscle toning effect is achieved by applying current to both of these muscles. The occurrence of dropping of the corners of the mouth due to aging and loss of muscular strength, and laughter lines, double chin, and face line sagging, can be improved by toning the zygomatic muscles.

The masseter muscles are muscles that are responsible for biting force, and fatigue can build up with chewing, teeth clenching etc. Also, there are problems such as a so-called square-jaw arising if masseter muscles are developed due to a person grinding their teeth, which may undesirably alter the shape of the face. Similarly, toning of masseter muscles by electrical stimulation etc., may cause undesirable shaping of the face, which results in an adverse effect in terms of cosmetology.

Application Method 1

With the present invention, in order to apply optimum stimulation to the zygomatic muscles and the masseter muscles, electrodes (160), (161), and (162) are arranged, and after adjusting the mask to a suitable position, current that has been controlled is applied between electrodes.

Figure 9:
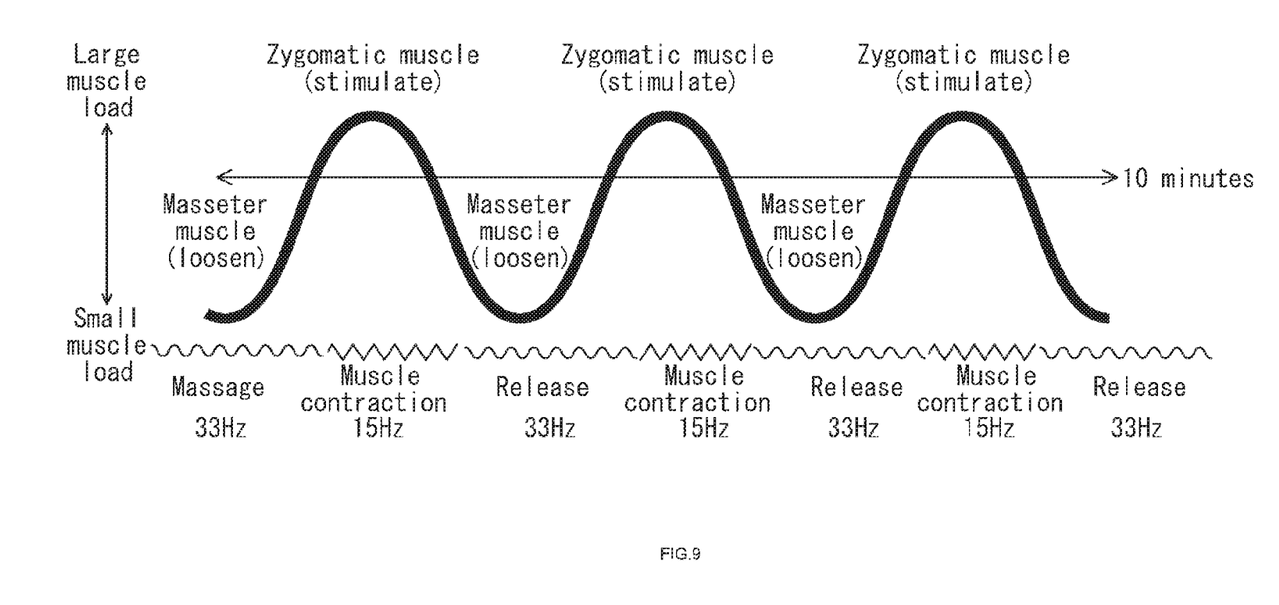
FIG. 9 is an explanatory drawing showing an example of electrical stimulation applied to zygomatic muscles and masseter muscles.

Specifically, electrical stimulation (30) at a suitable frequency for toning muscles is applied between the electrodes (160) and (161) corresponding to locations of the zygomatic muscles. As shown in FIG. 9, with this practical example low-frequency current of 15 Hz is applied.

Also, electrical stimulation (31) at a suitable frequency for easing muscles is applied between the electrodes (160) and (162) corresponding to locations of the masseter muscles. As shown in FIG. 9, with this practical example low-frequency current of 33 Hz is applied.

Then, the control section of the current generator (2) performs control to alternately apply current for masseter muscles and current for the zygomatic muscle and perform treatment for 10 minutes.

The scope of this invention is locations that provide stimulation to the zygomatic muscles and masseter muscles, discovered by the inventors from research. As shown in FIG. 8, the center position between electrodes (160) and (161) corresponding to locations of the zygomatic muscles is preferably at a position L1=76 mm±10 mm, particularly±5 mm, from the center of the face in a lateral direction, and L2=90 mm±10 mm, particularly±5 mm, from the lower end of the mask section (10), that is, in an upward direction from a position corresponding to the chin.

As shown FIG. 8, a center position between electrodes (160) and (162) corresponding to locations of the masseter muscles is preferably at a position of L3=109 mm±10 mm, particularly ±5 mm, from the center of the face in a lateral direction, and L4=63 mm 10 mm, particularly ±5 mm, from a lower end of the mask section (10), that is, in an upward direction from a position corresponding to the chin.

A distance between electrodes (160) and (161), and between electrodes (160) and (162) is preferably 60 mm+15 mm, and zygomatic muscles or masseter muscles between these electrodes are subjected to stimulation.

With a configuration equipped with the stimulator fitting section (16), openings at the above-described corresponding sections for arranging stimulators in the above-described range can be provided.

As a result of tests by the inventors, it was shown that relative values for size of laughter lines are reduced by about 12% by applying controlled low-frequency electrical current to zygomatic muscle locations for 10 minutes. Testing was conducted for three test subjects, and a tendency for improvement was seen in all subjects. Measurements were performed using an Antera 3D skin analyzer.

Application Method 2

The inventors performed more detailed tests, for current application methods, and found the optimum frequency for zygomatic muscles and masseter muscles. Results of these tests are shown in the following.

For three test subjects, electric currents of various frequencies were applied for 10 minutes in an environment of a room temperature of 250 and humidity of 38%, to measure degree of improvement in size and depth of wrinkles.

First, test results for zygomatic muscles are as shown in Table 1.

TABLE 1

| Frequency | Test subject 1 | | Test subject 2 | | Test subject 3 | |
|---|---|---|---|---|---|---|
| | size | depth | size | depth | size | depth |
| 1 Hz | x | x | x | r | x | x |
| 2 Hz | r | r | i | i | r | r |
| 5 Hz | i | i | i | i | i | i |
| 8 Hz | i | i | i | i | i | i |
| 10 Hz | i | r | i | i | i | i |
| 15 Hz | i | i | i | i | i | i |
| 20 Hz | r | r | i | i | i | i |
| 25 Hz | | | r | r | x | x |
| 33 Hz | x | x | x | x | x | x |
| 50 Hz | x | x | x | x | x | x |
| 100 Hz | x | x | x | x | x | x |
| 200 Hz | x | x | x | x | x | x | i: improvement; r: slight improvement; x: no improvement

The above test results show that a frequency applied to zygomatic muscles is effective in a range of 2 Hz to 20 Hz, and particularly in a range of 5 Hz to 20 Hz.

Further, it is also preferable to change application frequency over time in this frequency band. For example, the user can effectively apply electrical stimulation by repeatedly conducting control such as applying electricity at 10 Hz for 10 seconds, and then at 2 Hz for 10 seconds, so that the skin will not become accustomed to the electrical load.

Next, test results for masseter muscles are as shown in Table 2.

TABLE 2

| Frequency | Test subject 1 | | Test subject 2 | | Test subject 3 | |
|---|---|---|---|---|---|---|
| | size | depth | size | depth | size | depth |
| 1 Hz | x | x | x | x | x | x |
| 2 Hz | x | x | x | x | x | x |
| 5 Hz | x | x | x | x | x | x |
| 8 Hz | x | x | x | x | x | x |
| 10 Hz | x | x | x | r | x | x |
| 15 Hz | x | x | r | r | r | r |
| 20 Hz | r | r | i | i | i | i |
| 25 Hz | i | i | i | i | i | i |
| 33 Hz | i | i | i | i | i | i |
| 50 Hz | i | i | i | i | i | i |
| 100 Hz | i | i | i | i | i | i |
| 200 Hz | x | x | r | x | r | x | i: improvement; r: slight improvement; x: no improvement

The above described test results show that a frequency applied to masseter muscles is effective in a range of 20 Hz to 100 Hz.

Further, it is also effective to change application frequency over time in this frequency band. For example, the user can effectively apply electrical stimulation by repeatedly conducting control such as applying electricity at 100 Hz for 10 seconds and then at 20 Hz for 10 seconds, so that the skin will not become accustomed to the electrical load.

The cosmetic mask (1) of the present invention is formed of silicone as has been described above, and in particular, the mask section (10), the horizontal band (11), and the vertical band (12) are integrally formed. It is conventionally known to form a mask using silicone, but with the present invention it is particularly proposed to use silicone of differing hardness for each location.

Figure 10:
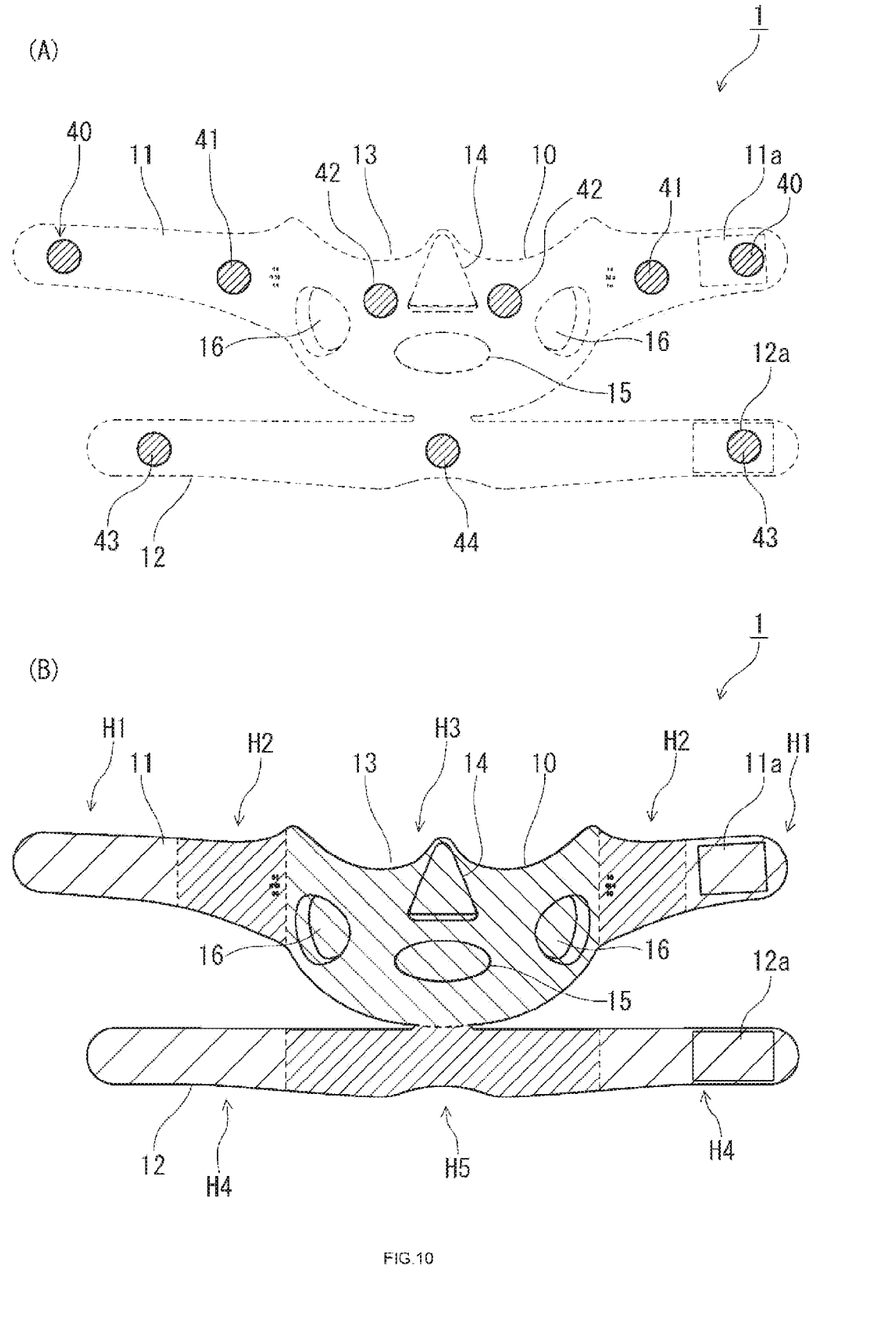
FIG. 10 is an explanatory drawing showing a formation method of the mask body of the present invention.

FIG. 10 is a drawing describing a method of molding the cosmetic mask (1). In FIG. 10(A), silicone materials (40) to (44) of differing hardness are arranged on a mold for forming the cosmetic mask (1), and the mask is formed by direct pressure molding with an upper mold and a lower mold while integrating the materials.

The silicone material (14) is placed on both ends of the horizontal band (11), to form a material having a rubber hardness of 200 that is easily stretchable. Similarly, the silicone material (43) is used on both ends of the vertical band (12).

The silicone material (41) used at locations corresponding to side surfaces of the face, and silicone material (44) used at locations corresponding to lower parts of the cheeks are slightly harder materials, having a rubber hardness of 40°. While the above-described locations impart a gentle touch due to their moderate elasticity, friction with the skin may arise when degree of elasticity is large, and a slightly less elastic material compared to the silicone materials (40), (43) is used at the band sections.

Further, a silicone material (42) having the highest degree of hardness, namely a hardness of 60°, is used in the mask section (10). A material of sufficient hardness is adopted because the above-mention location applies an appropriate tensile force to the face, and also in order to prevent the stimulator fitting section (16) from deforming, and reliably hold the current generator (2).

As a result of molding the cosmetic mask using silicone materials (40) to (44) of differing hardness, the cosmetic mask (1) having different hardness (H1) to (H5) depending on location is completed, as shown in FIG. 10(B). Regarding the above described hardness, hardness H1 and H4 20°, hardness H2 and H5 are 40°, and hardness H4 is 60°.

The above described strengths may be changed arbitrarily. For example, the horizontal band (11) the vertical band (12) may be configured having comparatively low hardness, while the mask section (10) may be configured having comparatively high hardness.

In this way, by changing the hardness of the materials, as well as contributing to improvement in usability of the cosmetic mask, it is possible to achieve a simple structure and reduced cost, and to realize a neat appearance in an integral design.

A specific usage for the cosmetic mask of the present invention is described as follows.

After face washing, condition and sufficiently moisturize the skin using such as skin-care products and lotion. Then apply cosmetic mask (1) to the face, wrap the horizontal band (11) and the vertical band (12) around so as to lift up the cheeks. Fit the previously charged current generator (2) into the cosmetic mask (1) and turn on the current of the current generator (2).

Operate the adjustment buttons (21) and (22) at a preferred strength chosen from six levels, for example. The cosmetic mask automatically turns off after 10 minutes of treatment.

According to the present invention, the cosmetic mask made of highly elastic silicone shapes up the face line by physically lifting up jaw lines, the mouth, and face line. Maintaining an ideal face line state, electrical current is output from a main body, and facial expression muscles are automatically toned. Toning of facial expression muscles is difficult, and it has been conventionally difficult to obtain ideal effects. According to the present invention, electrodes that are predetermined arranged around the laughter lines, the eyes, and the jaw, efficiently contract appropriate muscles. Further, since frequency of electrical current is controlled for each muscle, treatment can be given in a comfortable and effective manner.

Since the current generator is detachable, maintenance such as charging and cleaning, is easy. Also, since the cosmetic mask has no electrical cord, the person wearing it can move around in a room and even do housework.

While description of this practical example has been given as above, change is arbitrarily possible within the scope of the claim descriptions.

For example, the stimulators do not need to be detachable, and may be configured integrally with the mask. As stimulators, only one of either the zygomatic muscle stimulators or the masseter muscle stimulators may be provided, and electrodes may also be provided to tone other muscles, for example, the orbicularis orris or the musculus orbicularis oculi.

Although electrical current to be applied can be any of a low-frequency, medium frequency, or high-frequency, as has been described above, it is necessary to set respectively optimum currents in accordance with the nature of a muscle, using the control section. For example, no electrical stimulation is applied to the venter frontalis muscle, corrugator muscle, or ridge of the nose, that would cause discomfort with low frequency being applied, or control is performed so as to apply electrical current of the frequency that will not cause discomfort. It also keeps laughing muscles from being applied with electrical stimulation which would cause pain if the user wears silver crowns.

The above-mentioned prior art publications disclose configurations to apply electrical current on a general area of the cheeks. However, the configuration that the intensity level or mode of the stimulation is preferably regulated.

The present invention attains these goals, leading to a significant esthetic effect.

What is claimed is:
1. A cosmetic mask configured to be worn on the face of a user and to cover at least the user's cheeks, the cosmetic mask comprising:
   a mask body configured for the face, the mask body including
   a stimulator mounting section, wherein the stimulator mounting section includes an aperture disposed at a location on the mask corresponding to one of the user's cheeks; and
   a stimulator attached to the stimulator mounting section, the stimulator including:
   a current generator comprising:
   a power supply button,
   one or more adjustment buttons,
   a feed section including a rechargeable battery and a feed terminal, for feeding power to the rechargeable battery wherein the rechargeable battery is configured to provide electrical current,
   a control unit configured to control the electrical current at a frequency for electrical stimulation,
   a skin-side electrode that is configured to contact a skin surface of the user and apply the electrical current to locations corresponding to the user's zygomatic muscles or masseter muscles,
   a device-side electrode that provides the electrical current to the skin-side electrode, and a mask-side electrode that provides the electrical current to the device-side electrode when the current generator is mounted in the stimulator mounting section, and wherein the current generator is integrally attachable to and detachable from the stimulator mounting section.

2. The cosmetic mask according to claim 1, wherein the mask body further comprises:

a nosepiece configured to conform to at least a convex shape of a nose of the user.

3. The cosmetic mask according to claim 1, wherein the mask body further comprises:

fitting sections that are configured to fit the user's face by applying a tensile force at least in a horizontal direction on the user's face.

4. The cosmetic mask according to claim 3, wherein the mask body is made of a material that has a hardness that is greater than a hardness of the fitting sections.

5. The cosmetic mask according to claim 1, wherein the mask body further comprises:

fitting sections that are configured to fit the user's face by applying a tensile force at least in a vertical direction on the user's face.

6. The cosmetic mask according to claim 5, wherein the mask body is made of a material that has a hardness that is greater than a hardness of the fitting sections.

7. The cosmetic mask according to claim 1, wherein the frequency for electrical stimulation is between 2 Hz and 100 Hz.

8. The cosmetic mask according to claim 1, wherein the frequency for electrical stimulation is between 20 Hz and 100 Hz.

9. The cosmetic mask according to claim 1, wherein the mask body is formed using a resin material, and wherein a hardness of the resin material is varied across different locations on the mask body.

* * * * *